United States Patent [19]

Beranek

[11] Patent Number: 4,598,708

[45] Date of Patent: Jul. 8, 1986

[54] TORQUE CLAMP FOR USE WITH PERVENOUS LEAD HAVING FIXATION DEVICE

[75] Inventor: William J. Beranek, Cooper City, Fla.

[73] Assignee: Cordis Corporation, Miami, Fla.

[21] Appl. No.: 651,428

[22] Filed: Sep. 17, 1984

[51] Int. Cl.$^4$ .............................................. A61B 19/00
[52] U.S. Cl. ................................. 128/303 R; 128/346;
128/419 P; 128/785; 81/177.3; 81/487
[58] Field of Search ............... 128/325, 326, 346, 354,
128/419 P, 642, 303, 785; 24/30.5 S, 530, 545,
557, 563; 81/177.3, 487

[56] References Cited

U.S. PATENT DOCUMENTS

| | | | |
|---|---|---|---|
| 3,616,497 | 11/1971 | Esposito | 128/346 |
| 3,974,834 | 8/1976 | Kane | 128/419 P X |
| 4,271,846 | 6/1981 | Little | 128/785 |
| 4,471,777 | 9/1984 | McCorkle | 128/419 P X |
| 4,523,590 | 6/1985 | Roth et al. | 128/325 |

Primary Examiner—Dalton L. Truluck
Attorney, Agent, or Firm—Henry W. Collins; Thomas R. Vigil

[57] ABSTRACT

A torque clamp utilized for actuating a fixation device of a pervenous lead into the myocardium of a heart comprises a body. The body includes opposed jaw portions and a jaw actuating mechanism which is opposite the jaw portions and which can be squeezed to open the jaws for gripping a terminal pin of the lead.

18 Claims, 3 Drawing Figures

TORQUE CLAMP FOR USE WITH PERVENOUS LEAD HAVING FIXATION DEVICE

BACKGROUND OF THE INVENTION

1. Field of the Invention

The present invention relates to a torque clamp for use with a pervenous pacing lead which is provided with a fixation device. The torque clamp can be used to actuate the fixation device. More particularly, the torque clamp is adapted to engage a terminal pin of the lead and is used to turn the fixation device thereon in a clockwise or counterclockwise direction to fix or remove, respectively, the fixation device from the myocardial wall of a heart chamber.

2. Description of the Prior Art

Heretofore various methods of actuating a fixation device of a pervenous pacing lead having a fixation device have been proposed.

For example, a plastic, plier-like device has been provided which is designed specifically for use with certain fixation devices.

Further, non-dedicated instruments such as hemostats have been utilized for actuation of fixation devices. A lead terminal pin is grasped by the instrument for rotation of the lead for actuating the fixation device to either embed itself within tissue or to extract itself from tissue.

As will be described in greater detail hereinafter, the torque clamp of the present invention provides a simple means for grasping the terminal pin of the lead assembly having a fixation device thereon. The torque clamp prevents slippage between the clamp and the terminal pin and scratching of the terminal pin, which scratching could damage the pin leading to corrosion of the pin. Further, by preventing slippage between the clamp and the terminal pin, improper or inadequate advancement of the fixation device, which could cause premature dislodgement of the device, is avoided.

SUMMARY OF THE INVENTION

According to the invention there is provided a torque clamp utilized for actuating a fixation device of a pervenous lead into the myocardium of a heart. The clamp comprises a body, including opposed jaw portions forming a jaw and a jaw actuating mechanism.

Preferably the jaw is defined by a stepped slot which extends into the body from a rounded periphery thereof and a terminal pin is adapted to be received in a stepped portion of the slot. The jaw actuating mechanism includes a flexible bridge portion in the body opposite the jaw portions. The body has two fingerholes on opposite sides of the slot and a cutaway space between the jaw portion and the bridge portion.

Further according to the invention there is provided a method for using the torque clamp including the steps of: placing fingers in the fingerholes; flexing the bridge portion inwardly with pressure being applied by a thumb to the bridge portion to cause outward flexure of the jaw portions; placing a terminal pin of a pervenous pacing lead within the stepped portion of the slot; and then releasing pressure on the bridge portion to allow the jaw portions to close and entrap the terminal pin of the pervenous pacing lead within the stepped portion of the slot.

DESCRIPTION OF THE PREFERRED EMBODIMENT

Figure 1:
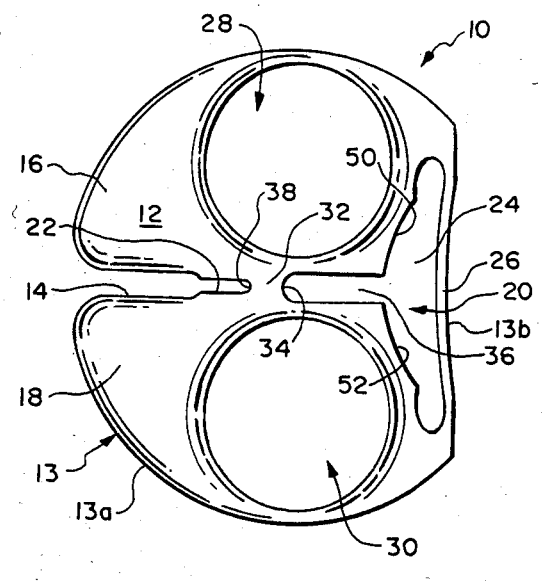
FIG. 1 is a top plan view of the torque clamp of the present invention.

Referring now to the drawings in greater detail, there is illustrated in FIG. 1 the torque clamp 10 of the present invention. The clamp 10 is fabricated of a polycarbonate material such as the material sold under the trademark Lexan, by either machining or molding.

As shown, the torque clamp 10 comprises a planar body 12 which has a split-hoof shape and a periphery 13. In this respect, approximately ¾ of the periphery 13 of the body 12 is curved or rounded as indicated at 13a while the other approximately ¼ periphery has a generally linear, slightly concave peripheral edge 13b.

The body 12 also has a stepped slot 14 extending inwardly from the center of the curved portion 13a of the periphery 13 to provide the split-hoof shape. The slot 14 also provides the clamp 10 with two jaw forming portions 16 and 18, one on each side of the slot 14.

The body 12 has a T-shaped cutaway space 20 which has somewhat of a goblet shape and extends toward the stepped portion 22 of the slot 14 with a cupped portion 24 of the cutaway space 20 facing the slightly concave linear peripheral edge 13b.

The provision of the cutaway space 20 provides a small bridge 26 of material along the linear periphery 13b of the body 12 which flexes when pressure is applied thereto and acts as an actuating member 26 for the clamp 10.

The body 12 has juxtaposed on either side of the slot 14 two circular fingerholes 28 and 30. A hinge 32 is formed between these fingerholes 28 and 30 and between an inner end 34 of a goblet stem portion 36 opposite an inner end 38 of the slot 14.

Figure 2:
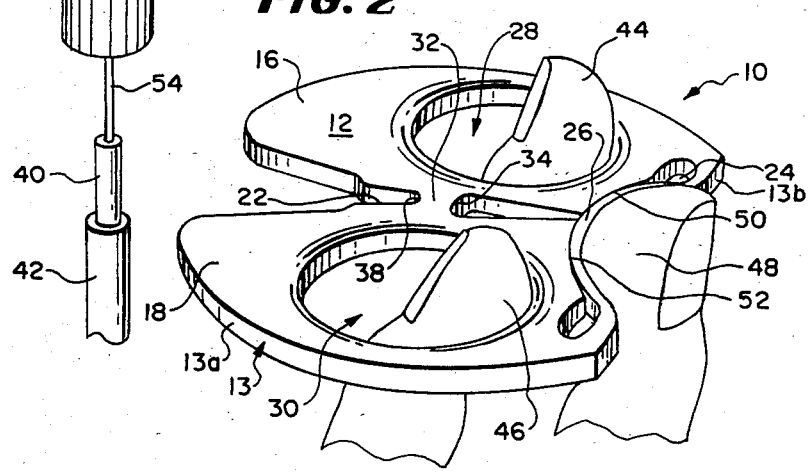
FIG. 2 is a perspective view of the torque clamp shown in FIG. 1 as it is being actuated to receive a terminal pin at the end of a pacing lead.

The method of using the clamp 10 to engage a terminal pin 40 of a pervenous lead 42 within the stepped portion of the slot 14 is illustrated in FIG. 2.

As shown the surgeon places two fingers 44 and 46 of his hand within the fingerholes 28 and 30 and places his thumb 48 along the bridge portion 26 of the clamp body 12. When pressure is applied against the bridge portion 26 by the surgeon's thumb, as shown, the bridge portion 26 flexes inwardly into the cupped portion 24 of the cutaway space 20 with the inward excursion of the bridge portion 26 being limited to stop edge portions 50 and 52 defining part of the cutaway space 20. The edges of the stem 34 of the cutaway space 20 fold inwardly as well, causing parts of the body 12 of the clamp 10 to pivot apart around the hinge 32 so as to pull the jaw portions 16 and 18 apart opening the slot 14 into a V-shaped opening.

Once the slot 14 is in this V-shaped position, the surgeon may feed a terminal pin 40 of a pervenous lead 42 through the slot 14 and into the stepped portion 22 thereof. The lead 42 may have a corkscrew shaped fixation device (not shown) on the distal end thereof and the lead 42 may or may not incorporate a stiffening stylet 54 received through the terminal pin 40 and within the body of the pervenous lead 42.

Figure 3:
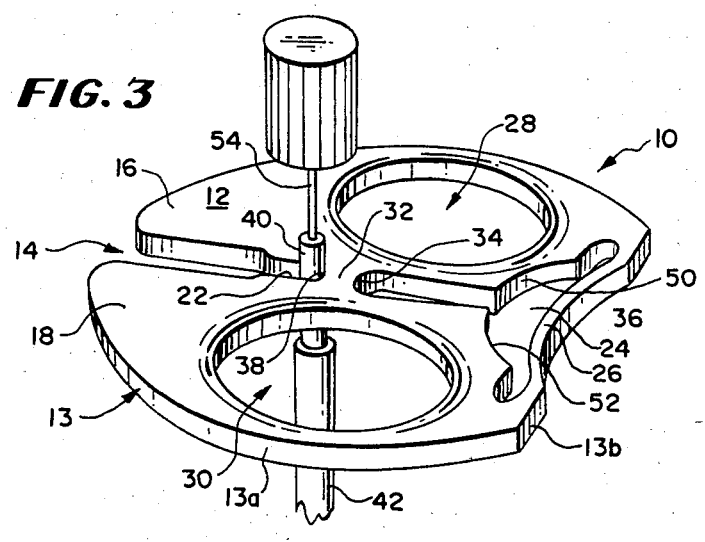
FIG. 3 is a perspective view of the torque clamp similar to FIG. 2 and shows the terminal pin gripped by the torque clamp.

As illustrated in FIG. 3, when the surgeon releases pressure on the bridge portion 26, the slot 14 reverts to its original narrow slot position and entraps the terminal pin 40 of the pervenous lead 42 within the stepped portion 22 thereof.

Once the terminal pin 40 is securely received within the stepped portion 22, the torque clamp 10 is rotated in a clockwise direction to rotate the pin 40 in a clockwise direction to advance the fixation device (not shown) into myocardial tissue within a heart chamber, such as the ventricle, to anchor the lead 42 therein. The anchoring of the lead 42 can be verified by fluoroscopy.

Once the anchoring of the lead 42 is effected, the flexible bridge portion 26 is depressed again causing the jaws 16 and 18 of the torque clamp 10 to open thereby releasing the terminal pin 40 from engagement therein.

For retraction of the fixation device from the myocardial tissue, the clamp 10 is once again placed around the terminal pin 40 as described above, but is now rotated in a counterclockwise direction to rotate the pin 40 counterclockwise thereby to detach the fixation device from the myocardial tissue.

As described above, the torque clamp 10 of the present invention has a number of advantages, some of which have been described above and others of which are inherent in the invention. For example, the torque clamp 10 grasps the terminal pin 40 of the pervenous lead 42 firmly so no slippage takes place between them such as is incurred with the use of non-dedicated instruments. Such slippage causes inadequate advancement of the fixation device into the myocardium which may cause premature detachment of the fixation device. Further, damage by scratching of the terminal pin 40 by a non-dedicated instrument such as a hemostat is eliminated thereby ensuring a long useful life for the terminal pin 40 and lead assembly 42.

Also, modifications can be made to the torque clamp 10 of the present invention without departing from the teachings of the present invention. Accordingly, the scope of the invention is only to be limited as necessitated by the accompanying claims.

I claim:

1. A torque clamp utilized for actuating a fixation device at the distal end of a pervenous lead to anchor the fixation device in the myocardum of a heart by rotation of a terminal pin of the pervenous lead comprising: a body, said body including opposed jaw portions, a jaw being defined between said jaw portions and jaw actuating means comprising a flexible bridge portion formed in said body opposite said jaw portions, said body having a cutaway spaced between an inner side of said bridge portion and said jaw portions, having a hinge portion between said jaw and said cutaway space, and having body portions on either side of said cutaway space, said bridge portion being deflectable into said cutaway space to cause deflection of said jaw portion away from each other about said hinge portion and concurrent deflection of said body portions toward each other.

2. The torque clamp of claim 1 wherein said body is fabricated of a polycarbonate.

3. The torque clamp of claim 1 being a unitary one piece clamp.

4. The torque clamp of claim 2 wherein said clamp is a machined piece of polycarbonate.

5. The torque clamp of claim 1 wherein said clamp is a molded piece of polycarbonate.

6. The torque clamp of claim 1 wherein said body is generally planar.

7. The torque clamp of claim 1 wherein said body has a split-hoof shape.

8. The torque clamp of claim 1 wherein said body is generally flat and the periphery of said body is approximately ¾ circular and approximately ¼ linear.

9. The torque clamp of claim 8 wherein said linear periphery is slightly concave.

10. The torque clamp of claim 1 wherein the jaw defined between said jaw portions is formed by a stepped slot which extends into said body from a rounded periphery thereof and which provides the body with a split-hoof shape.

11. The torque clamp of claim 10 wherein a stepped portion of said slot is adapted to receive and frictionally engage therein a terminal pin of a pervenous pacing lead.

12. The torque clamp of claim 1 wherein said body has two fingerholes therein which are juxtaposed to one another on each side of said slot.

13. The torque clamp of claim 1 wherein said cutaway space is T-shaped and has the general configuration of a goblet.

14. The torque clamp of claim 13 further comprising two stop formations for limiting the inward excursion of the flexible bridge portion into a cup portion of the goblet shaped cutaway space.

15. The torque clamp of claim 13 wherein said body portions adjacent a stem portion are location of said goblet shaped cutaway space and flex inwardly toward each other on inward movement of said bridge portion.

16. A method for using the torque clamp of claim 12 including the steps of: placing fingers in said finger holes; flexing said bridge portion inwardly with pressure being applied by a thumb to said bridge portion to cause outward flexure of said jaw portions; placing a terminal pin of a pervenous pacing lead within said stepped portion of said slot; and then releasing pressure on said bridge portion to allow said jaw portions to close and entrap the terminal pin of a pervenous pacing lead within said stepped portion of said slot.

17. The method of claim 16 including the step of rotating said torque clamp clockwise to cause advancement of a fixation device at the distal end of the pervenous lead into myocardial tissue.

18. The method of claim 16 including the step of rotating said torque clamp counterclockwise to cause retraction of a fixation device at the distal end of the pervenous lead from myocardial tissue.

* * * * *

UNITED STATES PATENT AND TRADEMARK OFFICE
CERTIFICATE OF CORRECTION

PATENT NO. : 4,598,708

DATED : July 8, 1986

INVENTOR(S) : William J. Beranek

It is certified that error appears in the above-identified patent and that said Letters Patent is hereby corrected as shown below:

Column 4, line 40, after "portions" insert -- are located --.

Column 4, line 40, after "portion" delete "are locations".

Signed and Sealed this

Twentieth Day of January, 1987

Attest:

DONALD J. QUIGG

Attesting Officer

Commissioner of Patents and Trademarks